(12) United States Patent
Crossman et al.

(10) Patent No.: US 8,336,155 B2
(45) Date of Patent: Dec. 25, 2012

(54) REPLACEMENT HEAD FOR ELECTRIC TOOTHBRUSH

(75) Inventors: Scott P. Crossman, Rockford, MI (US); Dai Xiaoguo, Wenzhou Zhejiang (CN)

(73) Assignee: Ranir, LLC, Grand Rapids, MI (US)

( * ) Notice: Subject to any disclaimer, the term of this patent is extended or adjusted under 35 U.S.C. 154(b) by 464 days.

(21) Appl. No.: 12/726,701

(22) Filed: Mar. 18, 2010

(65) Prior Publication Data

US 2010/0263147 A1 Oct. 21, 2010

Related U.S. Application Data

(60) Provisional application No. 61/171,278, filed on Apr. 21, 2009.

(51) Int. Cl.
*A46B 9/04* (2006.01)

(52) U.S. Cl. .................. 15/167.1; 15/22.2; 310/47

(58) Field of Classification Search ............... 15/167.1, 15/21.1, 22.1, 22.2; 310/46, 47
See application file for complete search history.

(56) References Cited

U.S. PATENT DOCUMENTS

| | | |
|---|---|---|
| 3,335,443 A | 8/1967 | Parisi |
| 3,375,820 A | 4/1968 | Kuris |
| 3,488,788 A | 1/1970 | Robinson |
| 3,535,726 A | 10/1970 | Sawyer |
| 3,676,218 A | 7/1972 | Sawyer |
| 3,828,770 A | 8/1974 | Kuris |
| 3,980,906 A | 9/1976 | Kuris |
| 4,192,035 A | 3/1980 | Kuris |
| 4,333,197 A | 6/1982 | Kuris |
| 4,991,249 A | 2/1991 | Suroff |
| 5,138,733 A | 8/1992 | Bock |
| 5,150,492 A | 9/1992 | Suroff |
| 5,247,716 A | 9/1993 | Bock |
| 5,311,632 A | 5/1994 | Center |
| 5,369,831 A | 12/1994 | Bock |
| 5,378,153 A | 1/1995 | Giuliani et al. |
| 5,546,624 A | 8/1996 | Bock |
| 5,613,259 A | 3/1997 | Craft et al. |
| 5,784,742 A | 7/1998 | Giuliani et al. |
| 6,845,537 B2 | 1/2005 | Wong |
| 6,918,300 B2 | 7/2005 | Grez et al. |
| 7,024,717 B2 | 4/2006 | Hilscher |
| 7,067,945 B2 | 6/2006 | Grez et al. |
| 7,086,111 B2 | 8/2006 | Hilscher |
| 7,207,080 B2 | 4/2007 | Hilscher |
| 2004/0255409 A1 | 12/2004 | Hilscher |
| 2005/0000044 A1 | 1/2005 | Hilscher |
| 2005/0011025 A1 | 1/2005 | Hilscher |
| 2007/0234493 A1 | 10/2007 | Hilscher |
| 2008/0010771 A1 | 1/2008 | Hilscher |
| 2008/0020351 A1 | 1/2008 | Hilscher |
| 2008/0020352 A1 | 1/2008 | Hilscher |
| 2008/0022469 A1 | 1/2008 | Hilscher |
| 2008/0022470 A1 | 1/2008 | Hilscher |
| 2008/0022471 A1 | 1/2008 | Hilscher |
| 2008/0022501 A1 | 1/2008 | Hilscher |
| 2008/0022503 A1 | 1/2008 | Hilscher |
| 2008/0028549 A1 | 2/2008 | Hilscher |
| 2008/0032265 A1 | 2/2008 | Hilscher |
| 2008/0034515 A1 | 2/2008 | Hilscher |

FOREIGN PATENT DOCUMENTS

DE 20321197 6/2006
(Continued)

*Primary Examiner* — William Gilbert
(74) *Attorney, Agent, or Firm* — Warner Norcross & Judd LLP

(57) ABSTRACT

A replacement head for an electromagnetic toothbrush drive includes a mechanical linkage assembly for converting linear drive motion into rotational movement of the brush head. The mechanical linkage assembly includes a fixed shaft and a lever arm that extend between a movable bottom member and a fixed top member, and a link member rotatably connected to the top member and the brush head. The lever arm pivots about a fulcrum formed in the top member, and engages the link member. When the bottom member oscillates as a results of the actuation of the electromagnet in the drive unit, the lever arm pivots about the fulcrum and drives the link member to rotate in an arc shaped pattern. The rotation of the link member consequently rotates the brush head.

20 Claims, 5 Drawing Sheets

FOREIGN PATENT DOCUMENTS

| | | |
|---|---|---|
| DE | 20321198 | 10/2006 |
| EP | 0576620 | 9/1998 |
| EP | 0695131 | 3/2000 |
| EP | 0625017 | 5/2000 |
| EP | 0781105 | 11/2004 |
| WO | 94/01054 | 1/1994 |
| WO | 03092534 | 11/2003 |
| WO | 03092535 | 11/2003 |
| WO | 04000156 | 12/2003 |
| WO | 2004054467 | 7/2004 |
| WO | 2005000149 | 1/2005 |
| WO | 2005058189 | 6/2005 |
| WO | 2005058190 | 6/2005 |
| WO | 2006067758 | 6/2006 |
| WO | 2007029201 | 3/2007 |
| WO | 2007122491 | 11/2007 |
| WO | 2008001302 | 1/2008 |

REPLACEMENT HEAD FOR ELECTRIC TOOTHBRUSH

BACKGROUND OF THE INVENTION

The present invention is directed to electric toothbrushes, and, more particularly, to a replacement head for an electric toothbrush having an electromagnetic drive unit.

One method for actuating the bristles, or other cleaning elements, of an electric toothbrush is an electromagnetic drive positioned within the handle portion of the toothbrush. The electromagnet can be actuated by a switch to oscillate at an operating frequency. A movable permanent magnet is positioned proximate to the electromagnet, such that the permanent magnet is driven to oscillate at an oscillating frequency by the electromagnet when the electromagnet is actuated. An elongated neck including a brush head is typically attached to the permanent magnet, such that the brush head is driven to oscillate by the movement of the permanent magnet.

Recognizing the need to replace toothbrush bristles after they are worn out, manufacturers have designed replacement heads that fit onto separate electromagnetic drive units. The drive units typically include the power source, switch, and electromagnet, and the replacement heads typically include the permanent magnet and the brush head. The replacement heads can be removably attached to the drive units, for instance, by threading a portion of the replacement head onto a portion of the drive unit.

More recently, manufacturers have attempted to control the movement of the brush head and cleaning elements of electric toothbrushes, in order to provide a more desirable cleaning motion, such as rotational motion about the central longitudinal axis of the toothbrush. Difficulties arise in doing so, especially in the case of toothbrushes with electromagnetic drives, because the generally linear oscillation of the permanent magnets in the replacement head must be converted into the desired rotational motion. One replacement head for an electromagnetic drive toothbrush that converts linear drive motion into rotational motion of the brush head is disclosed in U.S. Pat. No. 7,067,945 to Grez. However, the replacement head disclosed by the Grez patent may add difficulty in manufacturing, because it requires spring members within the brush head that must each be tuned to a particular size and shape so that they twist when oscillated at a preselected frequency.

SUMMARY OF THE INVENTION

The present invention provides a replacement head for an electromagnetic toothbrush drive that includes a mechanical linkage assembly for converting linear drive motion into rotational movement of the brush head.

In one embodiment, the mechanical linkage assembly includes a fixed shaft and a lever arm that extend between a movable bottom member and a fixed top member, and a link member rotatably connected to the top member and the brush head. Permanent magnets are attached to the bottom member, such that the bottom member oscillates linearly when the electromagnet is actuated. The lever arm pivots about a fulcrum formed in the top member, and engages the link member. When the bottom member oscillates, the lever arm pivots about the fulcrum and drives the link member to rotate. The rotation of the link member consequently rotates the brush head.

In another embodiment, the fixed shaft is generally aligned with the central longitudinal axis of the toothbrush, and the lever arm is generally offset from the central axis. The fixed shaft may form a biasing member for returning the bottom member to a central position. The lever arm may include a ball positioned along the length of the lever arm for engaging a socket formed within the top member.

The present invention provides a mechanical assembly for converting the linear motion of the electromagnet into rotational motion of the brush head. Various parameters can be varied, such as the positioning of the fulcrum, to enable manufacturers to provide the brush head with a desired motion.

DETAILED DESCRIPTION OF THE CURRENT EMBODIMENTS

I. Overview

Figure 1:
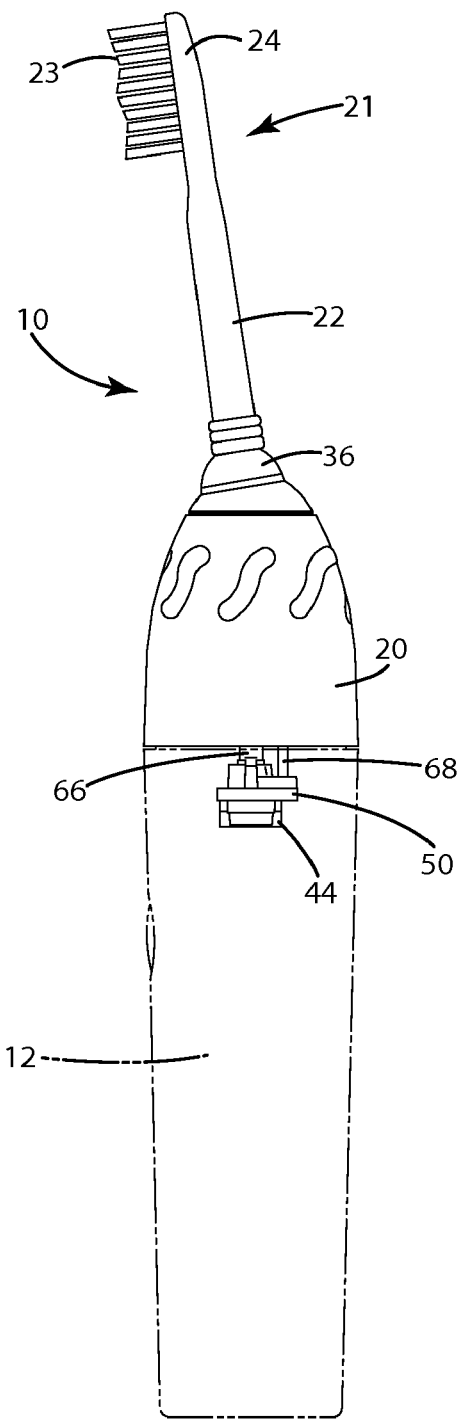
FIG. 1 is side view of an electric toothbrush including a replacement head according to one embodiment of the present invention.
Figure 2:
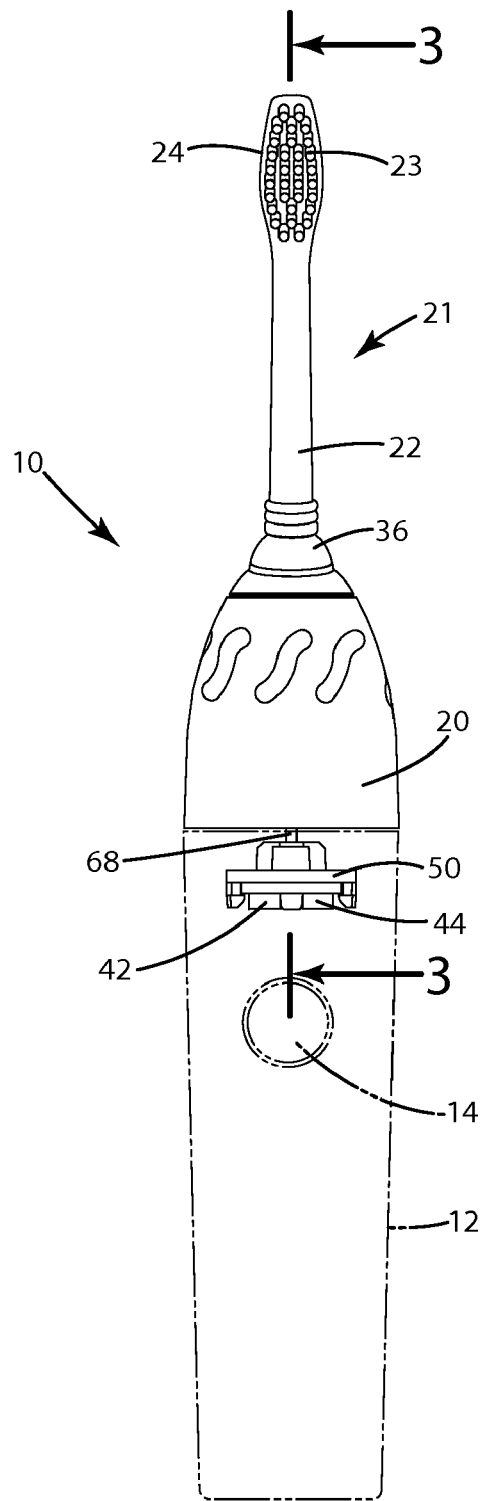
FIG. 2 is a front view thereof.

A replacement head for an electric toothbrush according to one embodiment of the present invention is shown in FIGS. 1-5 and generally designated 10. As illustrated, the replacement head 10 is designed for removable attachment to a drive unit, such as the electromagnetic drive unit 12 shown in FIGS. 1, 2 and 4.

II. Structure

As noted above, electromagnetic drive units are well known; therefore, the drive unit 12 will not be described in great detail herein. Suffice it to say that the drive unit 12 includes a power source, such as a battery or AC power supply, a switch 14 that is operable by the user, and an electromagnet (not shown) positioned within the drive unit 12 that is actuated when the user presses the switch 14. In one embodiment, the electromagnet is actuated to oscillate between positive and negative polarities within the drive unit 12. The drive unit 12 typically includes an opening at the upper end 16 that receives a portion of the replacement head 10. In one embodiment, the electromagnet is positioned within the drive unit 12 proximate to the upper end 16 such that it can magnetically engage and drive the replacement head 10. In addition, the drive unit 12 typically includes structure for removably attaching to the replacement head 10, and for aligning the replacement head 10 on the drive unit 12. In one embodiment, the drive unit 12 may include an upper cylindrical portion 18 at the upper end 16 that includes external threads (not shown) for attaching to a threaded housing 20 on the replacement head 10. The opening at the upper end 16 of the drive unit 12 may be shaped to align the replacement head on the drive unit 12 when the replacement head 10 is attached to the drive unit 12. In one embodiment, the opening is generally round, with one flat surface (i.e. D-shaped) that engages an opposing flat surface on a similarly shaped portion of the replacement head 10 to align the replacement head 10 and prevent rotation of the replacement head 10 with respect to the drive unit 12. Alternatively, the drive unit may include a rib or groove, or another conventional alignment structure, to receive corresponding structure on the replacement head.

Figure 3:
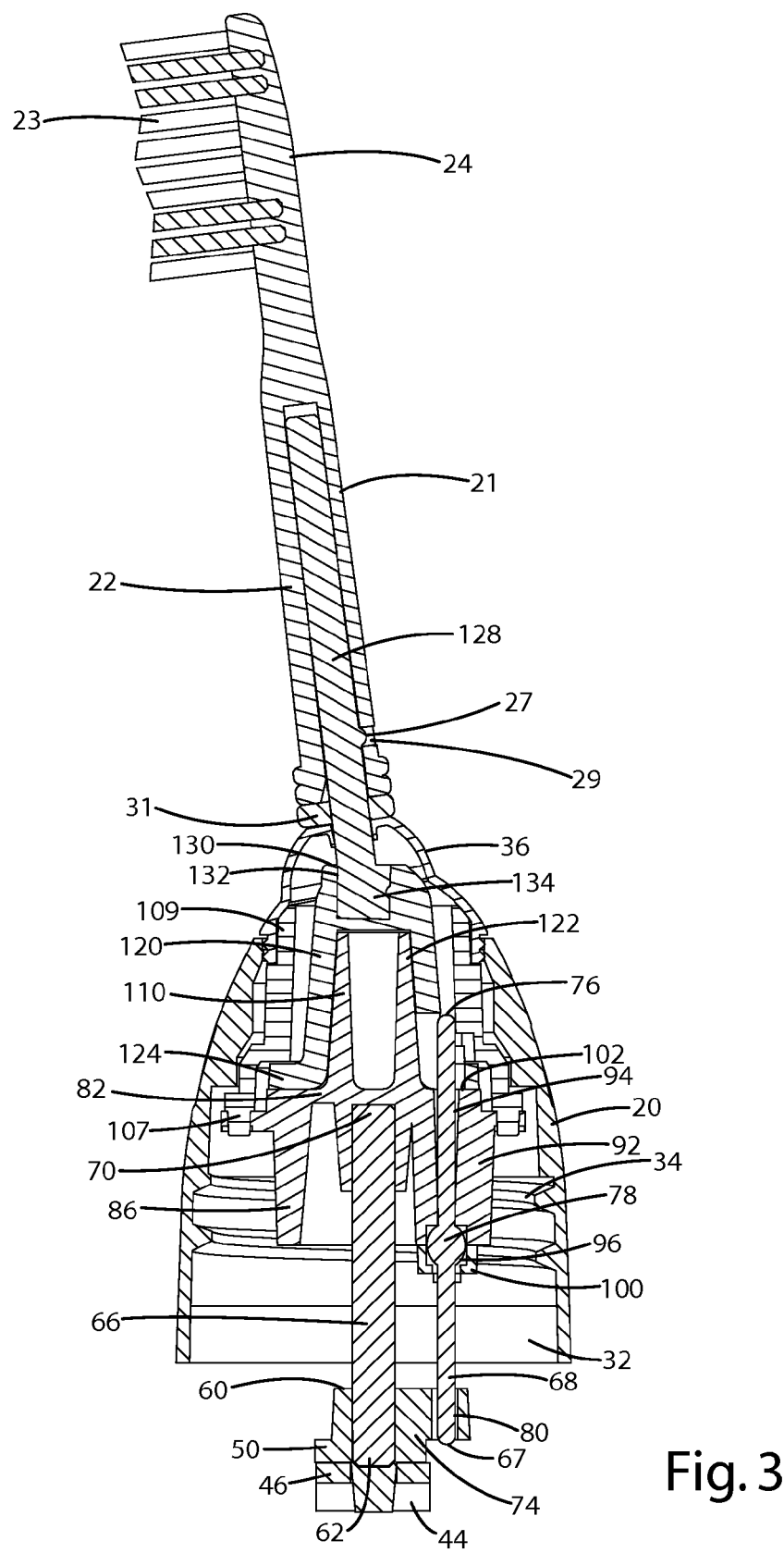
FIG. 3 is a side cross sectional view of a toothbrush head taken along line 3-3 in FIG. 2.
Figure 3A:
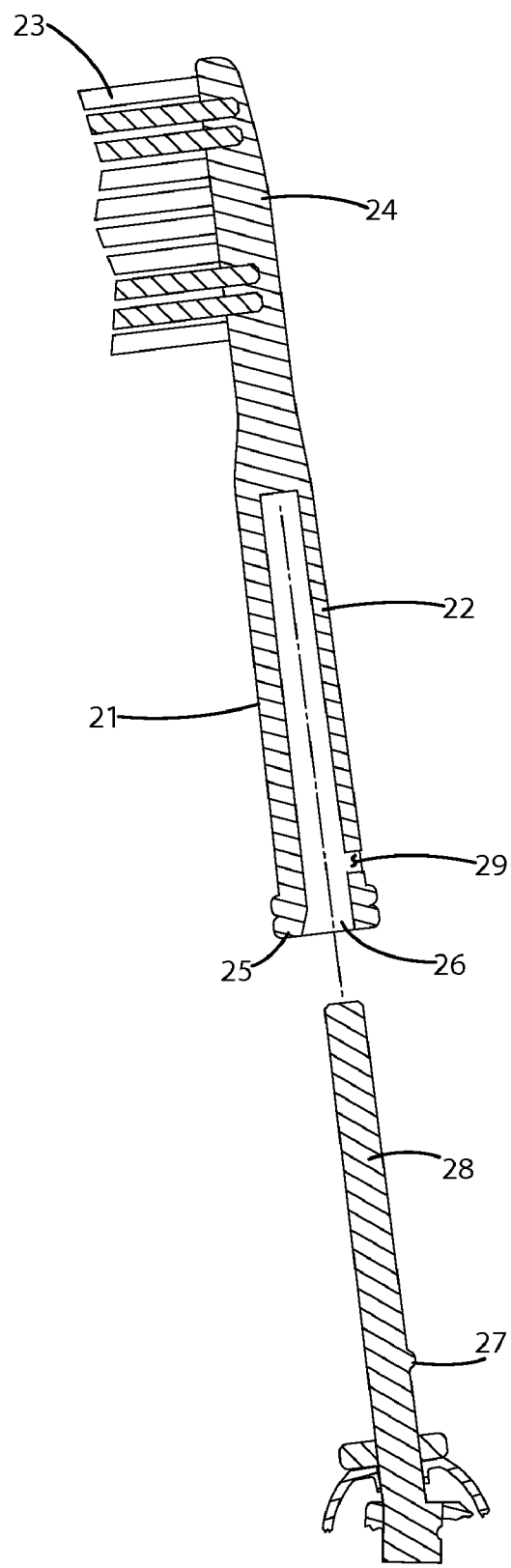
FIG. 3A is a side cross sectional view of a portion of the toothbrush head taken along line 3-3 in FIG. 2, with the bristle head removed.

The replacement head 10 generally includes a removable bristle head 21 having an elongated neck 22 with a head 24 at one end, a housing 20, and a mechanical linkage assembly 40 for converting the generally linear motion of the electromagnet into curvilinear motion at the head 24. As shown in FIG. 3A, one end 25 of the neck 22 of the replacement bristle head 21 defines an opening 26 for receiving a drive shaft 28. The drive shaft 28 may be slidably inserted into the opening 26, and, in one embodiment, the bristle head 21 is retained in place on the drive shaft by a detent 27 that fits within a notch or hole 29 in the neck 22. The bristle head 21 may be removed from the drive shaft 28 by pulling on the bristle head 21 to overcome the retention force of the detent 27 within the hole 29. In this embodiment, the bristle head 21 can be removed and replaced without replacing the entire toothbrush head 10. In another embodiment, the bristle head may be retained on the drive shaft with a frictional fit, or it may be more permanently secured with an adhesive or a mechanical attachment to the drive shaft 28. As illustrated, the head 24 includes a plurality of bristles 23 of various lengths extending outwardly from the head 24. In another embodiment, the head 24 may include one or more alternative cleaning elements, such as elastomeric elements, extending from the head 24.

The housing 20 is a shell that extends over the exterior of the mechanical linkage assembly 40. In the illustrated embodiment, the housing 20 includes an opening 32 that extends over the upper portion of the drive unit 12. The interior of the opening 32 includes a series of threads 34 for securing the housing 20 and the replacement head 10 to the drive unit 12. A sealing cap 36, made from a resilient material, may be fitted within the upper end of the housing 20 and extend between the housing 20 and the neck 22 to prevent water from entering the interior of the housing 20. In one embodiment, a sealing o-ring 31 may be positioned above the sealing cap 36 to further seal off the housing 20.

The mechanical linkage assembly 40 includes a pair of magnets 42, 44 (one positive, one negative) at one end, and the drive shaft 28 at the opposite end. When the replacement head 10 is attached to the drive unit, the magnets 42, 44 extend into the opening in the drive unit such that they are positioned proximate to the electromagnet within the drive unit 12. In one embodiment, the magnets 42, 44 are attached to a plate 46, for instance, with an adhesive, and the plate 46 is secured to the lower surface 48 of a bottom member 50 by a post 52 that extends through a hole 54 defined in the plate 46. Alternatively, the magnets could be attached directly to the bottom member 50. The bottom member 50 includes an outer periphery 51 that is smaller than the size of the opening within the drive unit 12, so that the bottom member 50 is capable of moving back and forth within the opening of the drive unit 12.

Figure 5:
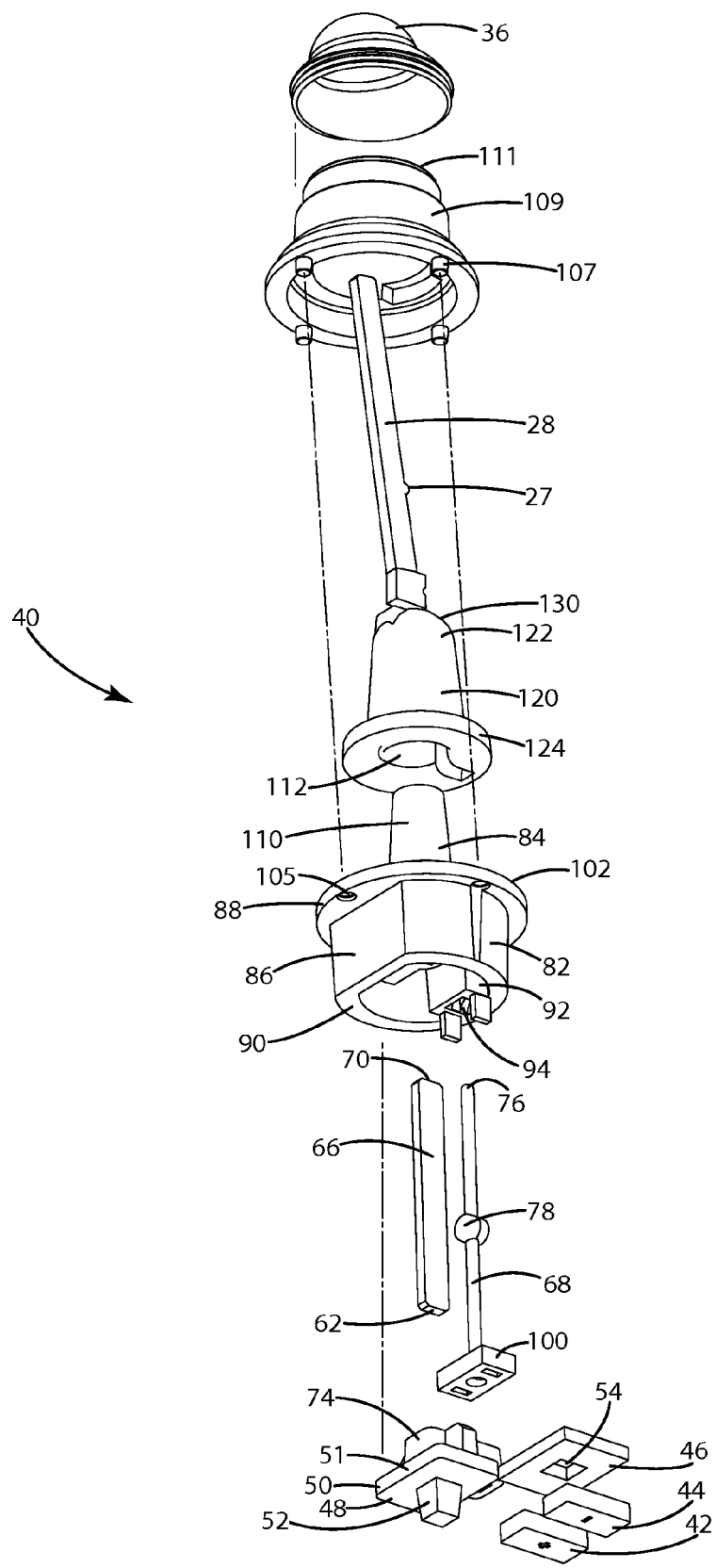
FIG. 5 is an exploded view of the mechanical linkage assembly.

The fixed shaft 66 extends between the bottom member 50 and a top member 82. As shown in FIGS. 3 and 5, the fixed shaft 66 is a rigid, elongated shaft with a first end 62 and a second end 70. In one embodiment, the shaft 66 is generally rectangular in cross-section, although other cross-sectional shapes may be used. The upper surface 60 of the bottom member 50 is configured to receive the first end 62 of the fixed shaft 66. The upper surface 60 of the bottom member 50 includes an upwardly extending boss 74 with an opening that receives the first end 62. In one embodiment, the opening in the boss 74 is shaped to correspond to the shape of the end 62 to prevent rotation of the first end 62 with respect to the bottom member 50. The second end 70 of the fixed shaft 66 extends into a slot 104 defined in the top member 82 and is fixedly secured in the slot 104. In one embodiment, the slot 104 is shaped similar to the cross-sectional shape of the fixed shaft 66 to prevent rotation of the shaft 66 with respect to the top member 82.

The lever arm 68 also extends between the bottom member 50 and the top member 82. As also shown in FIGS. 3 and 5, in one embodiment, the lever arm 68 is a generally cylindrical shaft with first and second rounded ends 67, 76, and a ball 78 positioned on the arm 68 at approximately the mid-point of the arm. As described in more detail below, the ball 78 forms a pivot point for the lever arm 68. The shape of the ball 78, the position of the ball on the lever arm 68, and the shape and length of the lever arm 68 can be varied depending on the desired pivot motion. In the illustrated embodiment, the first end 67 of the lever arm 68 is positioned within an opening 80 in the upper surface 60 of the bottom member 50 in an unsecured manner, such that the first end 67 is slightly movable within the opening 80. In one embodiment, the fixed shaft 66 extends generally coaxially with a central longitudinal axis of the drive unit 12 and the lever arm 68 is spaced from the fixed shaft and offset from the central axis. The fixed shaft 66 is oriented with the narrower dimension facing the lever arm 68, such that the it can bend about the thicker dimension as the magnets 42, 44 are driven linearly by the electromagnet; however, the orientation of the fixed shaft 66 may be varied as desired from application to application.

In one embodiment, the top member 82 includes an upper portion 84 and a lower portion 86. The lower portion 86 includes a lower surface 90 facing the bottom member 50 and is configured to receive both the fixed shaft 66 and the lever arm 68. With respect to the lever arm 68, the lower surface 90 includes a lever arm boss 92. As illustrated, the lever arm boss 92 defines a channel 94 that extends through the top member 82 and receives the lever arm 68. In one embodiment, a socket 96 is formed between the lower end of the boss 92 and a retainer 100. The socket 96 is sized and shaped to pivotally receive the ball 78 on the lever arm 68, and, in one embodiment, the socket 96 may be round to receive the spherical shaped ball 78. As shown, a hemispherical recess in the socket retainer 100 couples with a hemispherical recess in the boss 92 to form the socket 96. The retainer 100 further defines a hole to receive the lever arm 68. The retainer 100 may be snap-fitted, or otherwise attached, over the opening in the channel 94 to retain the ball 78 within the socket 96. Above the socket 96, the channel 94 in the top member 82 gradually widens to permit the lever arm 68 to pivot about the fulcrum formed by the socket 96. The width of the channel 94 can be varied to control the distance that the lever arm 68 is able to pivot. In one embodiment, when the lever arm 68 is inserted through the channel 94, the second end 76 extends above the upper surface 102 of the top member 82 to interfit with the link member 120 described below.

A flange 88 extends outwardly from the top member 82 and forms a stop that rests against the upper end 16 of the drive unit 12. As illustrated, the flange 88 defines a plurality of holes 105 for receiving protrusions 107 extending from an optional cap 109. The cap 109 includes a top edge 111 that interfits with the flexible sealing cap 36. When the housing 20 is secured to the drive unit 12, the flange 88 is held firmly against the drive unit 12, which holds the top member 82 in a fixed position with respect to the drive unit 12.

Figure 4:
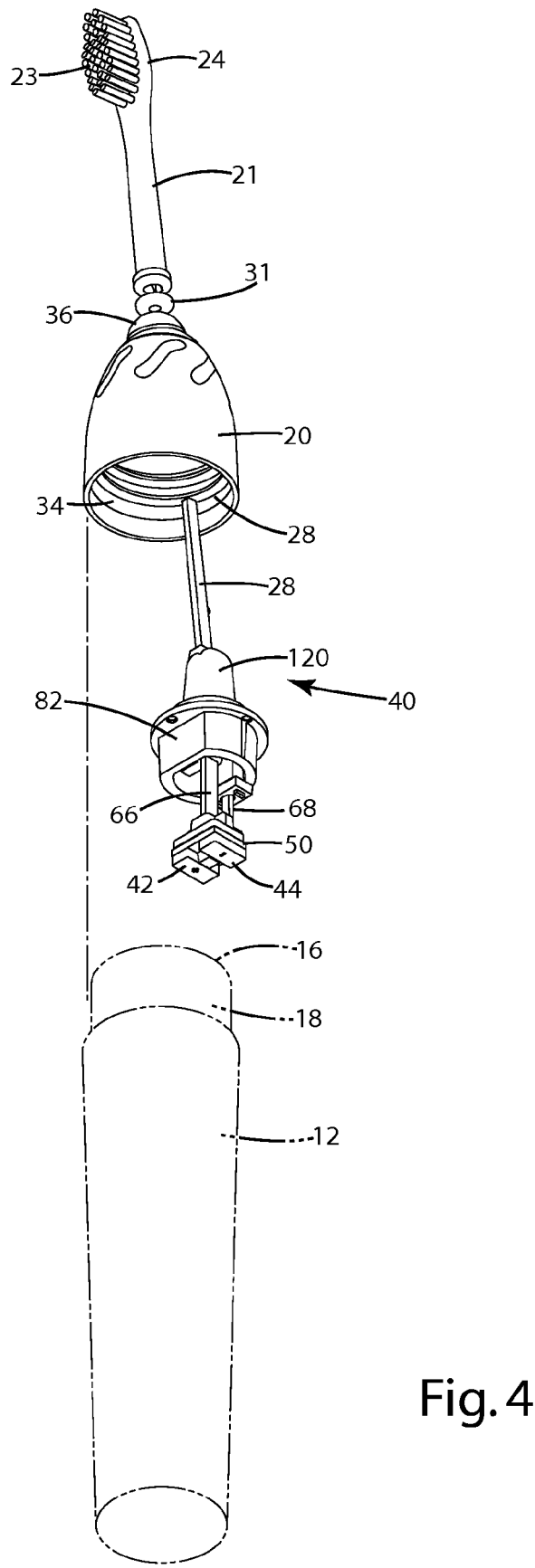
FIG. 4 is an exploded view of an electric toothbrush including a replacement head according to one embodiment of the present invention.

As shown in FIG. 3, the upper portion 84 of the top member 82 includes a protrusion 110, which, in the illustrated embodiment, is generally frustoconical. The protrusion 110 extends into a similarly shaped recess 112 in the bottom of a link member 120 positioned on the upper surface 102 of the top member 82. As shown in FIGS. 3-5, the link member 120 includes a generally frustoconical upper portion 122 extending from a generally cylindrical flange 124. In one embodiment, the flange 124 and a portion of the upper portion 122 define an opening 126 that receives the end 76 of the lever arm 68 such that movement of the lever arm 68 also moves the link member 120. The frustoconical protrusion 110 on the top member 82 fits into the recess 112 in the link such that the link member 120 can rotate about the protrusion 110, and thus rotate about the central longitudinal axis defined by the drive unit 12 when driven by the lever arm 68. The upper portion 122 of the link 120 includes an upper surface 130 that defines an opening 132 for receiving the lower end 134 of the drive shaft 28. In an alternative embodiment, the end 76 of the lever arm may include a ball attached to the lever arm 68 or formed as part of the lever arm 68 that fits into a socket on the link member 120 shaped to receive the ball to enable rotation of the ball within the socket. The inclusion of this ball and socket may reduce noise when the device is actuated.

III. Operation

In operation, the replacement head 10 is connected to a drive unit 12 by inserting the bottom member 50, including magnets 42, 44, into the opening in the upper end 16 of the drive unit 12. The housing 20 may be secured to the drive unit 12, for instance, with the internal threads 34 on housing 20, to hold the components of the replacement head 10 in place on the drive unit 12. When the head 10 is secured to the drive unit 12, the switch 14 can be actuated by the user to initiate the oscillation of the polarity of the electromagnet at a desired operating frequency. The oscillation of the electromagnet, and its attraction to the permanent magnets 42, 44 on the bottom member 50, causes the bottom member 50 to oscillate linearly.

When the bottom member 50 oscillates, the first end 62 of the fixed shaft 64 and the first end 67 of the lever arm 68 also oscillate linearly. The fixed shaft 62, being securely attached to both the bottom member 50 and the top member 82, acts as a biasing member to return the bottom member to a center position, generally aligned with the central longitudinal axis defined by the drive unit 12. The lever arm 68 pivots about the fulcrum created by the ball 78 and socket 96, and the movement of the second end 76 of the lever arm 68 in the opening 126 drives the link member 120 to rotate back and forth with respect to the top member 82. As a result of the rotation of the link member 120, the neck 22, head 24 and bristles 26 are driven to rotate back and forth in a similar manner. The mechanical linkage assembly 40 therefore mechanically converts the linear motion of the bottom member 50 into rotational motion of the brush head 24 and bristles 26. As noted above, the frequency and amplitude of the rotation of the brush head 24 can be controlled to desired levels by varying one or more of a number of parameters, such as the location of the ball 78 on the lever arm 68, the diameter of the lower portion 124 of the link member 120, and the width of the opening 94 extending through the top member 82.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The invention claimed is:

1. A replacement head for a toothbrush drive, the toothbrush drive including an electromagnet, the replacement head comprising:
    a housing connected to the toothbrush drive;
    a brush head connected to said housing;
    a top member fixedly attached to said housing;
    a link member connected to said brush head;
    a movable bottom member including at least one magnet attached to said bottom member, said at least one magnet positioned relative to said electromagnet when said housing is connected to the toothbrush drive such that said bottom member oscillates when the electromagnet is actuated; and
    a mechanical linkage assembly including a fixed shaft and a lever arm, said fixed shaft fixedly connected to said top member and said bottom member, said lever arm engaging said bottom member, said top member and said link member, wherein said lever arm is capable of pivoting about said top member and driving said link member to rotate said link member with respect to said housing, said rotation of said link member rotating said brush head.

2. The replacement head of claim 1 wherein said fixed shaft is generally aligned with a central longitudinal axis of the replacement head, and said lever arm is offset from said central longitudinal axis.

3. The replacement head of claim 1 wherein said lever arm includes a ball positioned along said lever arm, and wherein said top member includes a socket shaped to receive said ball.

4. The replacement head of claim 1 wherein one of said link member and said top member includes a protrusion, and the other of said link member and said top member includes an opening receiving said protrusion such that link member is capable of rotating with respect to said top member.

5. The replacement head of claim 4 wherein said link member defines a receptacle, and said pivot arm includes a first end engaging said bottom member and a second end extending into said receptacle.

6. The replacement head of claim 5 wherein said fixed shaft is rectangular in cross section, wherein the longer dimension of said rectangular cross section is aligned with said pivot arm, and the shorter dimension is perpendicular to said pivot arm.

7. The replacement head of claim 1 including a brush shaft attached to said top member, said brush head including a neck that defines an opening for receiving said brush shaft such that said brush shaft may be slidably inserted and removed from said opening.

8. A replacement head for an electromagnetic toothbrush drive, comprising:
    a fixed portion capable of attaching to said toothbrush drive, said fixed portion including a socket;
    a movable portion including at least one magnet;
    a brush head portion rotatably connected to said fixed portion, said brush head portion including a brush head having a plurality of tooth cleaning elements extending therefrom; and
    a lever arm including a first end engaging said movable portion and a second end engaging said brush head portion, said lever arm extending through said socket and capable of pivoting with respect to said socket, said lever arm driving said brush head portion to rotate upon oscillation of said movable portion.

9. The replacement head of claim 8 including a fixed shaft fixedly secured between said fixed portion and said movable portion, said fixed shaft extending along an axis of rotation of said brush head portion, said lever arm spaced from said axis or rotation.

10. The replacement head of claim 8 wherein said lever arm includes a ball positioned along the length of said lever arm, said socket shaped to receive said ball, said ball positioned within said socket.

11. The replacement head of claim 8 wherein one of said fixed member and said brush head member includes a protrusion and the other of said fixed member and said brush head member includes an opening shaped to mate with said protrusion, said protrusion extending into said opening.

12. The replacement head of claim 8 wherein said brush head member includes an elongated brush shaft and an elongated neck, said neck attached to said brush head and including an opening that slidably receives said brush shaft, said brush shaft and said neck including cooperating structure that enables said neck to snap fit onto said brush shaft.

13. A replacement head for an electromagnetic toothbrush drive unit, the drive unit including an electromagnet and a switch operable to actuate the electromagnet, the drive unit including an end defining an opening capable of receiving a portion of the replacement head, the replacement head comprising:
   a top member fixed with respect to the end of the drive unit;
   a movable member spaced from said top member and positioned within said opening in the drive unit, said movable member including at least one magnet capable of being oscillated generally linearly upon actuation of said electromagnet;
   a link member connected to said top member such that said link member is capable of rotating with respect to said top member;
   a brush head connected to said link member, said brush head including a plurality of tooth cleaning elements extending therefrom;
   a fixed shaft including a first end secured to said fixed member and a second end secured to said movable member; and
   a lever arm including a first end engaging said link member and a second end engaging said movable member, said lever arm capable of pivoting about a portion of said top member, wherein actuation of said electromagnet causes said first end of said lever arm to oscillate with said movable member, causing said second end of said lever arm to drive said link member and said brush head to rotate with respect to said top member.

14. The replacement head of claim 13 including a housing extending over said top member, said housing attached to said end of said drive unit.

15. The replacement head of claim 13 including a brush shaft extending from said link member and a neck extending from said brush head, said neck defining a receptacle and said brush shaft slidably inserted in said receptacle, wherein said brush shaft and said receptacle include cooperating structure that enables said brush shaft to snap fit into said receptacle.

16. The replacement head of claim 15 wherein said top member engages the top end of the drive unit and is held in place against the top end by said housing.

17. The replacement head of claim 16 wherein said top member includes a protrusion extending from said top member opposite said movable member, said link member defining a receptacle that receives said protrusions such that said link member is capable of rotating about said protrusion.

18. The replacement head of claim 17 wherein the toothbrush drive unit defines a central longitudinal axis, and said fixed shaft extends along said axis.

19. The replacement head of claim 18 wherein said lever arm is offset from said central longitudinal axis.

20. The replacement head of claim 19 wherein said link member includes am opening spaced from said receptacle, said opening receiving said first end of said lever arm.

* * * * *